(12) United States Patent
Kase et al.

(10) Patent No.: US 8,419,631 B2
(45) Date of Patent: Apr. 16, 2013

(54) ENDOSCOPE APPARATUS WITH FORWARD VIEWING AND SIDE VIEWING

(75) Inventors: Seigo Kase, Hino (JP); Yasuhito Kura, Hachioji (JP); Yuji Sakamoto, Kunitachi (JP)

(73) Assignee: Olympus Medical Systems Corp., Tokyo (JP)

( * ) Notice: Subject to any disclaimer, the term of this patent is extended or adjusted under 35 U.S.C. 154(b) by 165 days.

(21) Appl. No.: 13/052,599

(22) Filed: Mar. 21, 2011

(65) Prior Publication Data

US 2011/0282148 A1    Nov. 17, 2011

Related U.S. Application Data

(63) Continuation of application No. PCT/JP2010/068725, filed on Oct. 22, 2010.

(30) Foreign Application Priority Data

Nov. 6, 2009   (JP) .................................. 2009-255188

(51) Int. Cl.
*A61B 1/04*   (2006.01)
*A61B 1/012*  (2006.01)

(52) U.S. Cl.
USPC ............ 600/170; 600/157; 600/129; 600/109

(58) Field of Classification Search .................. 600/109, 600/118, 129, 168, 157, 170
See application file for complete search history.

(56) References Cited

U.S. PATENT DOCUMENTS

| 4,281,646 | A * | 8/1981 | Kinoshita ...................... 600/157 |
| 4,667,656 | A * | 5/1987 | Yabe ............................. 600/109 |
| 7,922,655 | B2 * | 4/2011 | Yasushi et al. ................ 600/173 |
| 8,226,551 | B2 * | 7/2012 | Sugimoto ...................... 600/170 |
| 2004/0254424 | A1 * | 12/2004 | Simkulet et al. .............. 600/176 |
| 2007/0203396 | A1 * | 8/2007 | McCutcheon et al. ........ 600/173 |
| 2008/0045797 | A1 * | 2/2008 | Yasushi et al. ................ 600/175 |
| 2009/0247830 | A1 * | 10/2009 | Miyamoto et al. ............ 600/157 |
| 2010/0081873 | A1 * | 4/2010 | Tanimura et al. ............. 600/109 |
| 2010/0091385 | A1 | 4/2010 | Togino |
| 2010/0195007 | A1 * | 8/2010 | Takahashi ....................... 349/16 |

FOREIGN PATENT DOCUMENTS

| EP | 1 769 718 A1 | 4/2007 |
| EP | 2 022 389 A1 | 2/2009 |
| EP | 0 2 106 739 A2 | 10/2009 |
| EP | 2 163 933 A1 | 3/2010 |

(Continued)

OTHER PUBLICATIONS

European Search Report dated Dec. 29, 2011 from corresponding European patent Application No. EP 10 82 8201.3.

*Primary Examiner* — John P Leubecker
(74) *Attorney, Agent, or Firm* — Scully Scott Murphy & Presser, PC

(57) ABSTRACT

An endoscope includes a side viewing observation section and a forward viewing observation section provided on a distal end side of an insertion portion which is inserted into an observation target for acquiring subject images of an observation target in a circumferential direction and an insertion direction of the insertion portion, respectively, a shielding section located within a viewing field of the side viewing observation section for shielding light from the subject entering the side viewing observation section and a protruding member protruding from the insertion portion arranged in a shielding region formed by the shielding section. The protruding member includes at least a cleaning nozzle for cleaning the forward viewing observation section and/or the side viewing observation section.

13 Claims, 10 Drawing Sheets

FOREIGN PATENT DOCUMENTS

| | | |
|---|---|---|
| JP | S57-90114 | 6/1982 |
| JP | 03-057441 | 3/1991 |
| JP | 10-165355 | 6/1998 |
| JP | 2000-116598 | 4/2000 |
| JP | 2001-154232 | 6/2001 |
| JP | 2003-070735 | 3/2003 |
| JP | 2004-195269 | 7/2004 |
| JP | 2008-309859 | 12/2008 |
| JP | 2008-309860 | 12/2008 |
| JP | 2008-309861 | 12/2008 |
| WO | WO 2006/004083 A1 | 1/2006 |
| WO | WO 2008/153114 A1 | 12/2008 |

* cited by examiner

ENDOSCOPE APPARATUS WITH FORWARD VIEWING AND SIDE VIEWING

CROSS REFERENCE TO RELATED APPLICATION

This application is a continuation application of PCT/JP2010/068725 filed on Oct. 22, 2010 and claims benefit of Japanese Application No. 2009-255188 filed in Japan on Nov. 6, 2009, the entire contents of which are incorporated herein by this reference.

BACKGROUND OF THE INVENTION

1. Field of the Invention

The present invention relates to an endoscope apparatus and an endoscope that enable forward viewing and side viewing observations.

2. Description of the Related Art

Endoscopes provided with illumination means and observation means on a distal end side of an insertion portion have been widely used in the medical and other fields in recent years.

The insertion portion of the endoscopes may be inserted into a tubular organ and used to inspect the inner wall thereof. To facilitate an inspection in such a case, endoscopes are being developed which are provided with not only a forward viewing field whose observation viewing field is a front side (distal end side) of the insertion portion along the axial direction (insertion direction) of the insertion portion but also amide viewing field whose observation viewing field is aside direction which is a side of the insertion portion or circumferential direction.

Japanese Patent Application Laid-Open Publication No. 2000-116598 as a first related art is provided with both viewing fields, but the side viewing field can only observe a range centered on a predetermined direction in a circumferential direction of the entire perimeter of 360°.

Japanese Patent Application Laid-Open Publication No. 2008-309860 as a second related art discloses an optical system of an endoscope provided with an optical system rotationally symmetric with respect to a central axis forming a forward viewing optical path that picks up an image of an object in the central axis direction and a wide-angle side viewing optical path (side viewing observation section) that produces at least two reflections in a ring-shaped optical device and forms an omnidirectional (entire sideward perimeter) ring-shaped image outside the circular image of the forward viewing optical path on the same image pickup device.

Furthermore, International Publication No. WO2006/004083 as a third related art discloses an endoscope attachment attached to a distal end portion of an endoscope provided with a forward viewing observation section and a wide-angle side viewing observation section.

The third related art describes a light-shielding structure to prevent illuminating light from entering the side viewing observation section.

SUMMARY OF THE INVENTION

An endoscope apparatus according to an aspect of the present invention includes an insertion portion inserted into an observation target, a side viewing observation section provided on a distal end side of the insertion portion for acquiring a subject image of an observation target in a circumferential direction of the insertion portion, a forward viewing observation section provided closer to the distal end side than the side viewing observation section of the insertion portion for acquiring a subject image of an observation target in an insertion direction of the insertion portion, a shielding section that forms a shielding region for electrically or mechanically shielding a display of part of the subject within a viewing field of the side viewing observation section, an image processing apparatus that generates a side viewing observed image and a forward viewing observed image including the shielding region as observed images based on the subject image in the circumferential direction obtained from the side viewing observation section and the subject image in the insertion direction obtained from the forward viewing observation section, and a protruding member arranged behind the shielding region and within the shielding region that protrudes from the insertion portion.

An endoscope according to another aspect of the present invention includes an insertion portion inserted into an observation target, a side viewing observation section provided on a distal end side of the insertion portion for allowing light from the observation target in a circumferential direction of the insertion portion to enter and acquiring a subject image, a forward viewing observation section provided closer to the distal end side than the side viewing observation section in the insertion portion for allowing light from the observation target in an insertion direction of the insertion portion to enter and acquiring a subject image, a shielding section located within a viewing field of the side viewing observation section that shields light from the subject entering the side viewing observation section, and a protruding member arranged within a shielding region formed by the shielding section that protrudes from the insertion portion.

BRIEF DESCRIPTION OF THE DRAWINGS

FIG. 16B is a diagram illustrating an example of endoscope image when mask processing is set to ON.

DETAILED DESCRIPTION OF THE PREFERRED EMBODIMENTS

Hereinafter, embodiments of the present invention will be described with reference to the accompanying drawings.
(First Embodiment)

Figure 1:
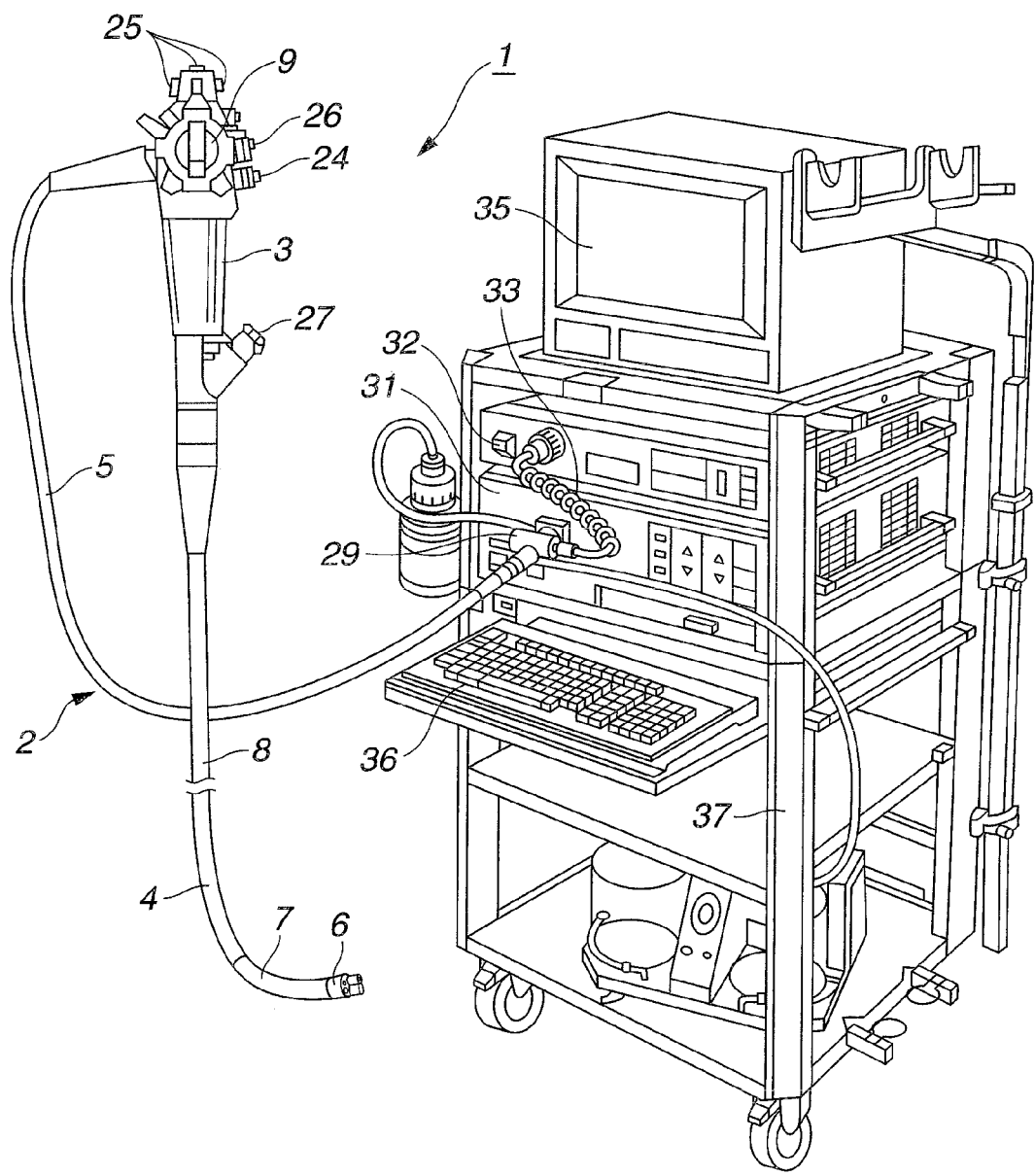
FIG. 1 is a perspective view illustrating an endoscope apparatus according to a first embodiment of the present invention.

As shown in FIG. 1, an endoscope apparatus 1 according to a first embodiment of the present invention has an endoscope 2 that performs endoscopy. The endoscope 2 is configured by including an operation section 3 grasped and operated by a surgeon, an elongated insertion portion 4 formed at a front end of the operation section 3 and inserted into an observation target such as the body cavity and a universal cord 5, a proximal end of which extends from one side of the operation section 3.

Furthermore, the insertion portion 4 is made up of a rigid distal end portion 6 provided at a distal end thereof, a bendable bending portion 7 provided at a rear end of the distal end portion 6 and a long flexible tube portion 8 provided at a rear end of the bending portion 7 and the bending portion 7 can be bent using a bending operation lever 9 provided at the operation section 3.

Figure 2:
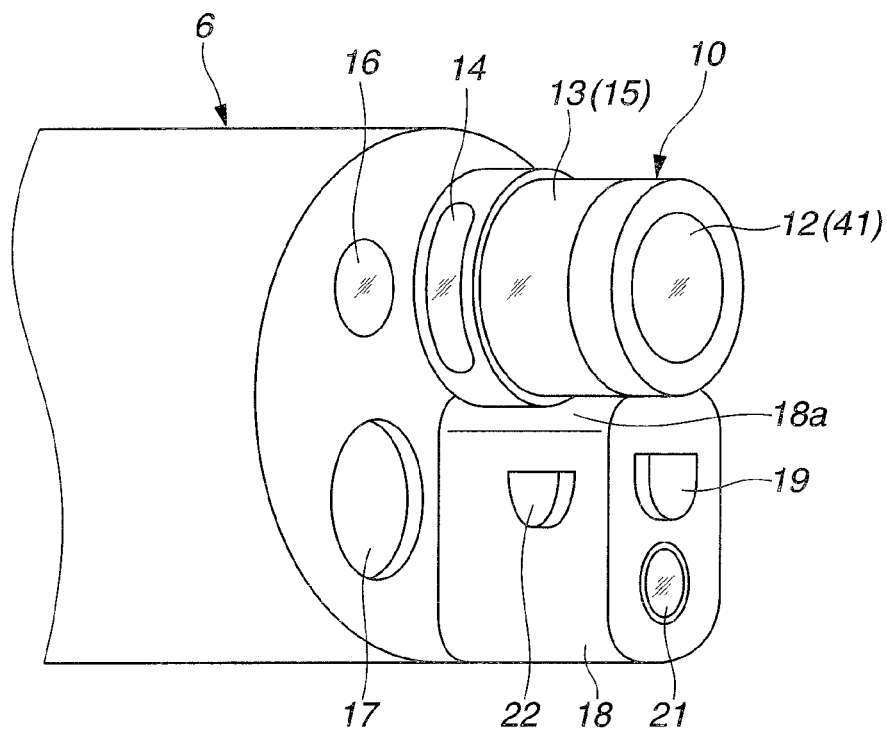
FIG. 2 is a perspective view illustrating a configuration of a distal end portion of an insertion portion of the endoscope.

Furthermore, as shown in FIG. 2, a cylindrical portion 10 protruding in a cylindrical shape from a distal end face of the distal end portion 6 at a position, for example, decentered upward from the center thereof is formed in the distal end portion 6 of the insertion portion 4. An objective optical system 11 (see FIG. 4) for both forward viewing and side viewing optical observations is provided in a distal end portion of the cylindrical portion 10, a forward viewing observation window 12 as a forward viewing observation section and a side viewing observation window 13 as a side viewing observation section are formed and a side viewing illuminating window 14 is formed in the vicinity of a proximal end of the cylindrical portion 10.

The side viewing observation window 13 has a side viewing field formed to have a wide angle so as to cover the entire perimeter in the side direction along a substantially ring-shaped side direction in the cylinder-shaped cylindrical portion 10 and is provided with a mirror lens 15 as a reflection optical system for capturing light from the subject within the side viewing field into the side viewing field and acquiring the light as a side viewing field image.

Furthermore, a forward viewing illuminating window 16 that emits illuminating light to the observation target side corresponding to the forward viewing field of the forward viewing observation window 12 neighboring the cylindrical portion 10 for illumination and a channel distal end opening portion 17 that serves as a distal end opening that allows a treatment instrument inserted in a channel to protrude are provided on the distal end face of the distal end portion 6.

Furthermore, in the present embodiment, a support portion 18 is provided neighboring, for example, a lower position in a circumferential direction of the cylindrical portion 10 so as to protrude from the distal end face of the distal end portion 6 to generate an excellent side viewing field image.

The support portion 18 is provided with a shielding section 18a that optically shields a protruding member making up the endoscope 2 which protrudes from the distal end face and which is not an original observation target, to prevent the protruding member from appearing within the side viewing field and being acquired as a side viewing field image.

The support portion 18 supports (or holds) a forward viewing observation window nozzle portion 19 as a nozzle for cleaning the forward viewing observation window 12 that protrudes from the distal end face of the distal end portion 6 and constitutes a protruding member appearing within the side viewing field and a forward viewing illuminating window 21 that likewise constitutes a protruding member, and shields the forward viewing observation window nozzle portion 19 and the forward viewing illuminating window 21 with the shielding section 18a so as not to appear in the side viewing field image.

Figure 3:
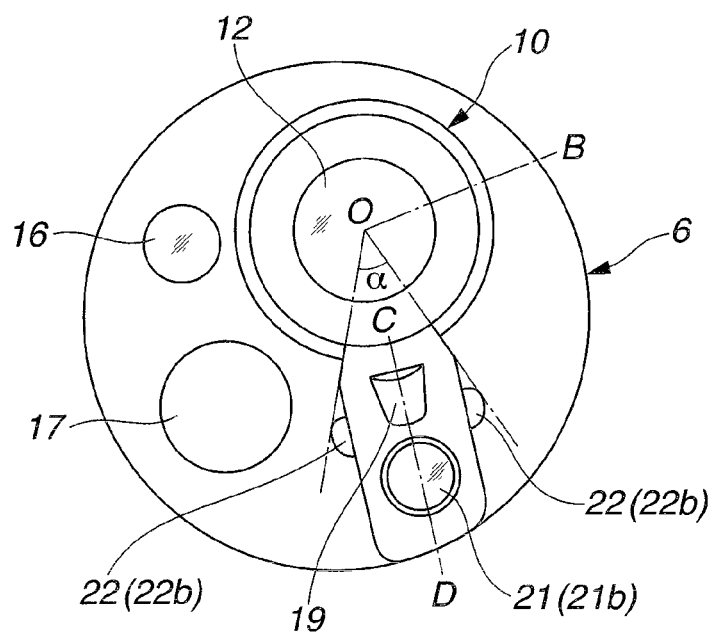
FIG. 3 is a front view illustrating a configuration of the distal end portion of the insertion portion.

Furthermore, the support portion 18 supports a side viewing observation window nozzle portion 22, a distal end of which protrudes from the side of the support portion 18 and opens to face the side viewing observation window 13 to function as a nozzle for cleaning the side viewing observation window 13 and also shields the side viewing observation window nozzle portion 22 so as not to appear in a side viewing field image. As shown in FIG. 3, the side viewing observation window nozzle portion 22 is provided in two locations.

The operation section 3 shown in FIG. 1 is provided with a gas/liquid feeding operation button 24 so as to allow the forward viewing observation window nozzle portion 19 and the side viewing observation window nozzle portion 22 to selectively inject a cleaning gas or liquid and the surgeon can switch between feeding gas and feeding liquid by operating the gas/liquid feeding operation button 24.

Although FIG. 1 illustrates an example where one gas/liquid feeding operation button 24 is provided, the function may be assigned to a scope switch 25 provided at the top of the operation section 3.

Furthermore, the operation section 3 is provided with a suction operation button 26 to suction and recollect mucus or the like in the body cavity through the channel distal end opening portion 17. The channel is formed of a tube (not shown) or the like disposed in the insertion portion 4 and communicates with a treatment instrument insertion port 27 provided near the front end of the operation section 3.

When performing a treatment using the treatment instrument, the surgeon inserts the treatment instrument from the treatment instrument insertion port 27, causes a distal end side thereof to protrude from the channel distal end opening portion 17 and can thereby perform a treatment using the treatment instrument.

Furthermore, a connector 29 is provided at an end of the universal cord 5 and the connector 29 is connected to a light source apparatus 31 of the endoscope. A pipe sleeve (not shown) which is a connection end of a fluid conduit protruding from a distal end of the connector 29 and a light guide pipe sleeve (not shown) which is a supply end for illuminating light are detachably connected to the light source apparatus 31 and one end of a connection cable 33 is connected to an electric contact portion provided on the side.

Furthermore, the connector of the other end of the connection cable 33 is electrically connected to a video processor 32 as a signal processing apparatus or image processing apparatus that performs signal processing or image processing with respect to an image pickup device 34 mounted in the endoscope 2.

The video processor 32 supplies a drive signal for driving the image pickup device 34 (see FIG. 4) mounted in the distal end portion 6 of the endoscope 2, performs signal processing on an image pickup signal (image signal) outputted from the image pickup device 34 with the supplied drive signal and generates a video signal.

The video signal generated by the video processor 32 is outputted to a monitor 35 as a display apparatus and an image picked up by the image pickup device 34 is displayed on the display surface of the monitor 35 as an endoscope image. The peripheral apparatuses such as the light source apparatus 31, the video processor 32 and the monitor 35 are arranged on a stand 37 together with a keyboard 36 for inputting patient information or the like.

The illuminating light generated by the light source apparatus 31 is transmitted through a light guide passed from the universal cord 5 through the operation section 3 and the insertion portion 4, radiated, radiatively spread out from the side viewing illuminating window 14 of the cylindrical portion 10 protruding from the distal end portion 6, the forward viewing illuminating window 16 and the forward viewing illumination window 21 (provided in the support portion 18) in the side direction and the insertion direction respectively so as to be able to illuminate a subject side such as a diseased part.

Figure 4:
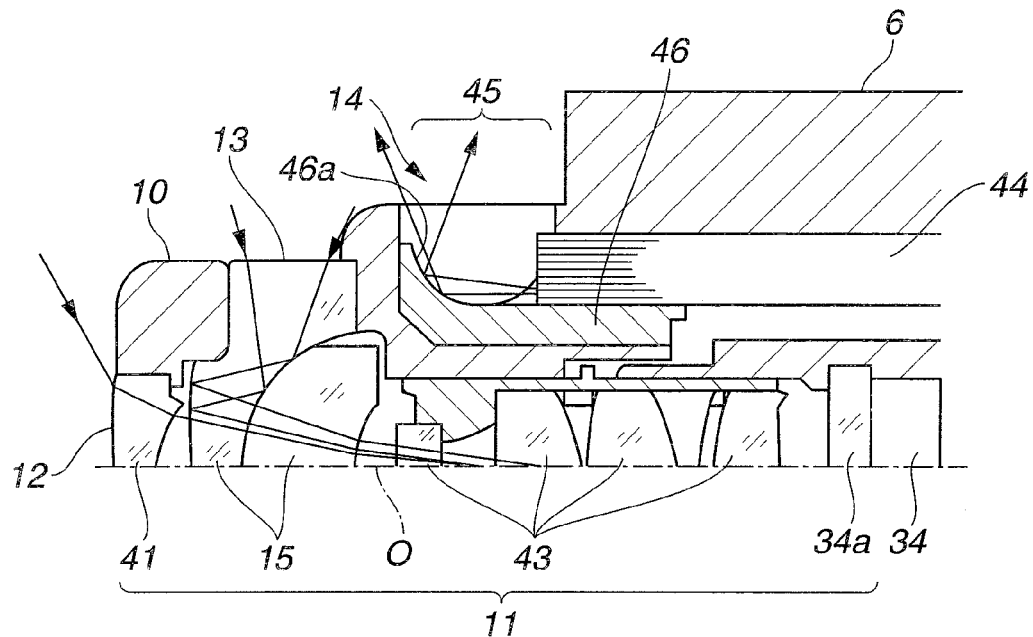
FIG. 4 is a cross-sectional view illustrating a perimeter of the objective optical system on an O-B cross section in FIG. 3 and a structure of the side viewing illuminating window.

FIG. 4 illustrates an O-B cross section of FIG. 3, that is, a configuration of peripheral sections of the objective optical system 11 which has dual forward viewing and side viewing functions, and the side viewing illuminating window 14.

The objective optical system 11 is formed on the optical axis that coincides with the image pickup center O along the central axis of the cylindrical portion 10 protruding from the distal end portion 6, made up of a front lens 41, the mirror lens 15 and a rear lens group 43, each of which is rotationally symmetric, being arranged to form an image on the image pickup device 34. A cover glass 34a is provided in front of the image pickup device 34.

The front lens 41 provided in the forward viewing observation window 12 as a circular forward viewing observation section at the distal end of the cylindrical portion 10 forms a wide-angle forward viewing field whose front side along the axial direction (insertion direction) of the insertion portion 4 corresponds to an observation viewing field.

The mirror lens 15 arranged immediately behind the front lens 41 is made up of two joined lenses and reflects light incident from the side twice by the joining surface and the front surface, and guides the reflected light to the rear lens group 43.

Using the mirror lens 15 provided in the side viewing observation window 13, the side viewing observation window 13 forms a quasi-ring-shaped observation viewing field that covers the entire perimeter in the insertion portion circumferential direction while maintaining a predetermined viewing angle substantially centered on the optical axis in the side viewing direction with respect to the insertion portion longitudinal axis direction.

As is obvious from FIG. 4, the forward viewing observation window 12 protrudes from the distal end face of the distal end portion 6 of the insertion portion 4 toward the distal end side more than the side viewing observation window 13 does.

FIG. 4 schematically shows paths of a light beam entering the front lens 41 forming the forward viewing observation window 12 from the subject side in the viewing field thereof and a light beam entering the mirror lens 15 forming the side viewing observation window 13 from the subject side in the viewing field thereof.

A subject image by light from the subject entering the viewing field of the front lens 41 of the forward viewing observation window 12 is formed in a circular shape in the center of the image pickup surface of the image pickup device 34 and acquired as a forward viewing field image. Furthermore, a subject image by light from the subject entering the viewing field of the mirror lens 15 facing the side viewing observation window 13 is formed in a ring shape on the circumferential side of the forward viewing field image and acquired as a ring-shaped side viewing field image.

However, in the present embodiment, the shielding section 18a of the support portion 18 mechanically shields part of ring-shaped side viewing field image as will be described later.

Furthermore, a distal end side of a light guide 44 as a light guide member for side viewing illumination is arranged on the peripheral side of the cylindrical portion 10, a light guide groove 45 is formed extending in a belt shape in the circumferential direction of the cylindrical portion 10 centered on a position that a distal end face of the light guide 44 faces and the light guide groove 45 is formed by arranging a reflection member 46 with a concave reflection section 46a provided in a notched recessed part for forming the light guide groove 45.

The light guide 44 and the light guide groove 45 formed of the reflection member 46 are arranged in a plurality of locations along the circumferential direction of the cylindrical portion 10. In this case, the distal end face of the light guide 44 as a light guide member is located near the center position in the circumferential direction of each reflection member 46 making up the light guide groove 45 formed in a belt shape along the circumferential direction of the cylindrical portion 10.

The light exited from the distal end face as a light exit end face of the light guide 44 is reflected by the reflection section 46a of the inner surface of the reflection member 46 (inner surface of the light guide groove 45) and the illuminating light is exited at a wide angle in the side direction in which the light guide groove 45 is provided.

The side viewing illuminating window 14 which exits the side viewing illuminating light over a wide range in the side direction is then formed of the light guide groove 45 made up of a plurality of light guides 44 and reflection member 46. Therefore, the observation target side portion corresponding to the viewing field of the entire perimeter in side direction which can be observed through the side viewing observation window 13 can then be illuminated with illuminating light exited from the side viewing illuminating window 14.

Furthermore, in the present embodiment, the forward viewing observation window nozzle portion 19 or the like disposed along the side viewing observation window 13 is supported by the support portion 18 and also shielded with respect to the side viewing field so as to be able to acquire an excellent side viewing field image.

As shown in FIG. 2 and FIG. 3, the support portion 18 has a substantially rectangular parallelepiped shape and is formed such that the rectangular parallelepiped top surface side portion contacts the side portion at the bottom end of the cylindrical portion 10.

The shielding section 18a (see FIG. 2) provided opposed to the side viewing observation window 13 so as to block the side viewing observation window 13 in the support portion 18 has a shielding function. The support portion 18 may be metal such as stainless steel forming the distal end portion 6 or may also be formed using resin such as polysulfone resin or the stainless steel outer circumferential side part may be covered with resin.

Furthermore, in the case of resin such as polysulfone resin, the shielding section 18a portion facing the side viewing observation window 13 may be made of a material containing a black paint to enhance the function of shielding light or the entire support portion 18 may have a black color.

The support portion 18 in the present embodiment not only has the function of shielding the protruding member such as the forward viewing observation window nozzle portion 19 or the like so as not to appear within the side viewing field of the side viewing observation window 13 but also supports the protruding member such as the forward viewing observation window nozzle portion 19 or the like and increases its mechanical strength.

For this reason, the present embodiment adopts a configuration in which the forward viewing observation window nozzle portion 19 or the like is arranged inside the support portion 18. As will be described later, a configuration provided only with the shielding function as in the case of embodiments may be adopted.

Figure 5:
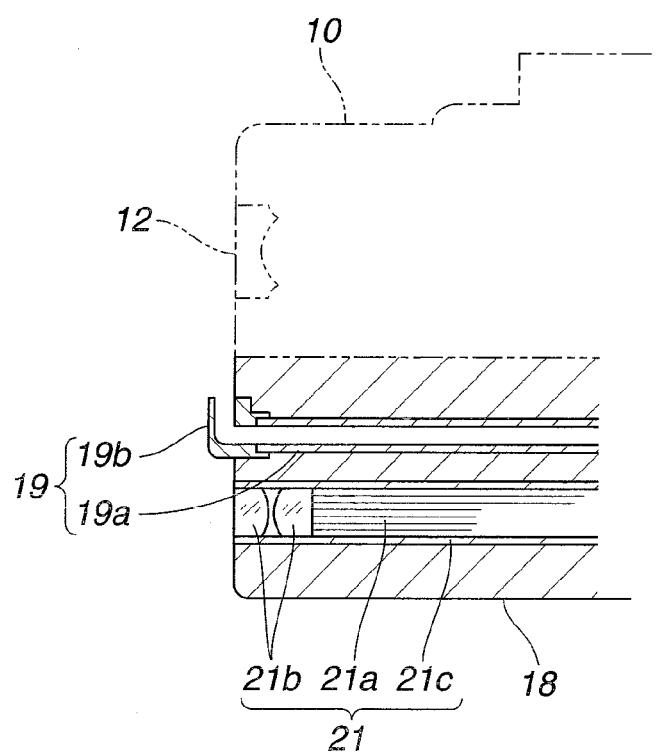
FIG. 5 is a diagram illustrating a protruding member such as a forward viewing observation window nozzle section arranged inside the shielding member according to a C-D cross section in FIG. 3.

In the interior of the support portion 18, a gas/liquid feeding conduit 19a is arranged as shown in FIG. 5 and a forward viewing observation window nozzle 19b which is bent in an L-figure shape and opens in the direction of the forward viewing observation window 12 side is provided at a distal end of the gas/liquid feeding conduit 19a and the forward viewing observation window nozzle portion 19 is formed.

The forward viewing observation window nozzle 19b changes the injection direction of gas or liquid sent from the gas/liquid feeding conduit 19a side to a substantially right angle direction, injects the gas or liquid to the forward viewing observation window 12 side to thereby wash adherents such as body fluid stuck to the forward viewing observation window 12 off the forward viewing observation window 12 and restore the forward viewing observation window 12 to a clean state.

Furthermore, a light guide 21a is arranged as a light guide member for illuminating light neighboring the forward viewing observation window nozzle portion 19 inside the support portion 18 and an illumination lens 21b is arranged at a distal end face of the light guide 21a, the light guide 21a and the illumination lens 21b forming the forward viewing illuminating window 21. The distal end side portion of the light guide 21a and the illumination lens 21b are fixed inside a tubular base 21c.

Light exited from the distal end face of the light guide 21a is made to exit from the forward viewing illuminating window 21 through the illumination lens 21b to the forward side thereof as illuminating light to illuminate the subject on the forward viewing field side of the forward viewing observation window 12. The distal end face of the support portion 18 is formed so as to be substantially positioned on the same surface with the distal end face of the cylindrical portion 10.

The side viewing observation window nozzle portion 22 is also made up of a gas/liquid feeding conduit (not shown) and a side viewing observation window nozzle 22b that opens toward the side viewing observation window 13 provided at a distal end thereof. The side viewing observation window nozzle 22b protrudes from the side surface of the support portion 18, but is mechanically shielded by the shielding section 18a (see FIG. 2) formed so as to block the side viewing observation window 13 in the support portion 18 to prevent the side viewing observation window nozzle 22b from being acquired as a side viewing field image.

The shielding section 18a mechanically shields an angle of α around an image pickup center O in the circumferential direction as shown in FIG. 3, and the forward viewing observation window nozzle portion 19, the forward viewing illuminating window 21 and the side viewing observation window nozzle portion 22 are arranged as protruding members within this angle α.

The endoscope 2 of the present embodiment having such a configuration is provided with the side viewing observation window 13 as a side viewing observation section for acquiring a subject within a side viewing field formed at a wide angle along the circumferential direction of the insertion portion 4 on the distal end side of the insertion portion 4 as a side viewing field image and the forward viewing observation window 12 provided closer to the distal end side than the side viewing observation window 13 in the insertion portion 4 as a forward viewing observation section for acquiring a subject within the forward viewing field along the axial direction of the insertion portion 4 as a forward viewing field image.

Furthermore, the endoscope 2 is provided with the forward viewing observation window nozzle portion 19 as a protruding member protruding toward the distal end side more than the side viewing observation window 13 passing through the side viewing field by the side viewing observation window 13, the forward viewing illuminating window 21, the side viewing observation window nozzle portion 22 and the shielding section 18a that shields the light from a range (predetermined range) in which at least the protruding member within the side viewing field passes so as not to enter the side viewing field (or side viewing observation section).

Figure 6:
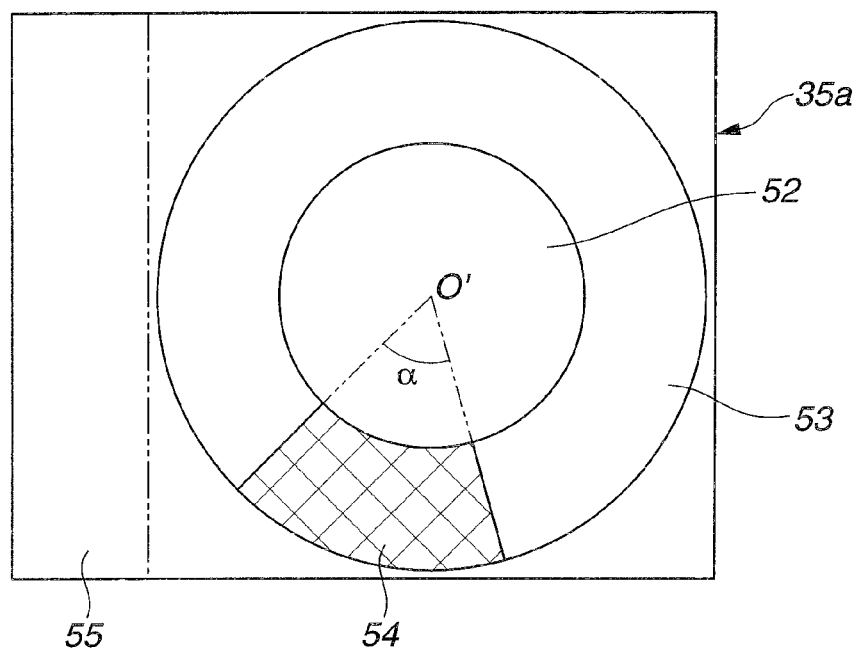
FIG. 6 is a diagram illustrating an example of an endoscope image according to the first embodiment.

FIG. 6 shows a display example where a subject image picked up by the image pickup device 34 using the endoscope 2 is displayed on a display surface 35a of the monitor 35 as an endoscope image.

A rectangular region 51 in FIG. 6 corresponds to a display region of the image pickup surface of the image pickup device 34. A center circular region of the rectangular region 51 corresponds to a display region 52 of the forward viewing field image by the forward viewing observation window 12 and a ring-shaped region outside the display region 52 corresponds to a display region 53 of a side viewing field image by the side viewing observation window 13.

Furthermore, a region where the shielding section 18a of the support portion 18 mechanically shields part of the side viewing field is formed as a shielding region 54 in the side viewing field image. The shielding region 54 is a region corresponding to the angle α in FIG. 3 around the image center O' corresponding to the image pickup center O in FIG. 3.

The surgeon can smoothly inspect a tubular organ or the like by observing an endoscope image.

According to the endoscope 2 of the present embodiment, the shielding section 18a provided in the support portion 18 can shield the light from the forward viewing observation window nozzle portion 19, the forward viewing illuminating window 21 and the side viewing observation window nozzle portion 22, which are protruding members as components of the endoscope 2 different from the original observation targets, appearing within the side viewing field of the side viewing observation window 13 so as not to be acquired as a side viewing field image. The endoscope 2 of the present embodiment can shield the protruding members different from the original observation targets and can acquire a side viewing field image corresponding to the original observation target.

Furthermore, according to the present embodiment, even when an image signal of the image pickup device 34 is used for automatic light adjustment, a light adjustment signal for automatic light adjustment can be generated from an image signal not affected by the protruding members, and automatic light adjustment can thereby be effectively used without deterioration of the function.

(Second Embodiment)

Figure 7:
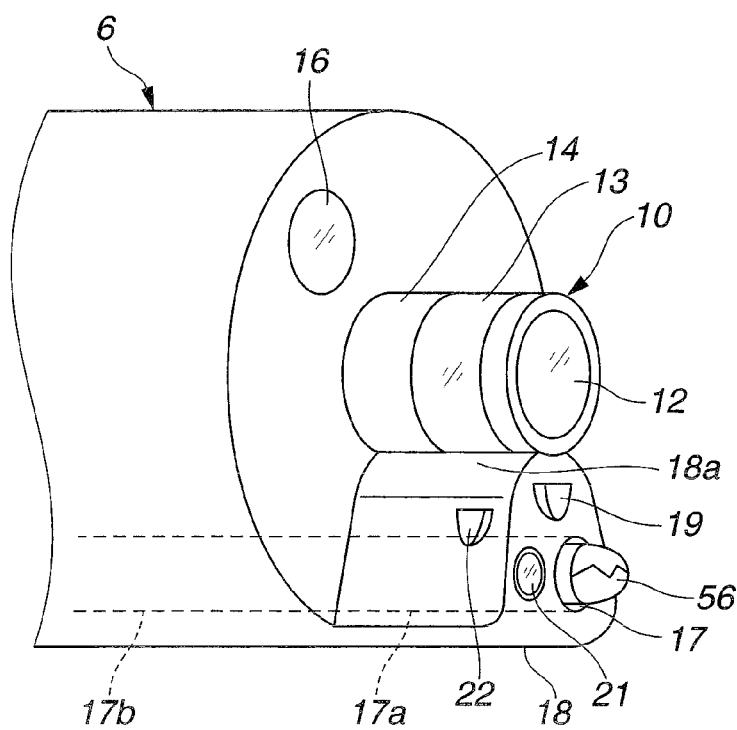
FIG. 7 is a perspective view illustrating a configuration of a distal end portion according to a second embodiment of the present invention.
Figure 8:
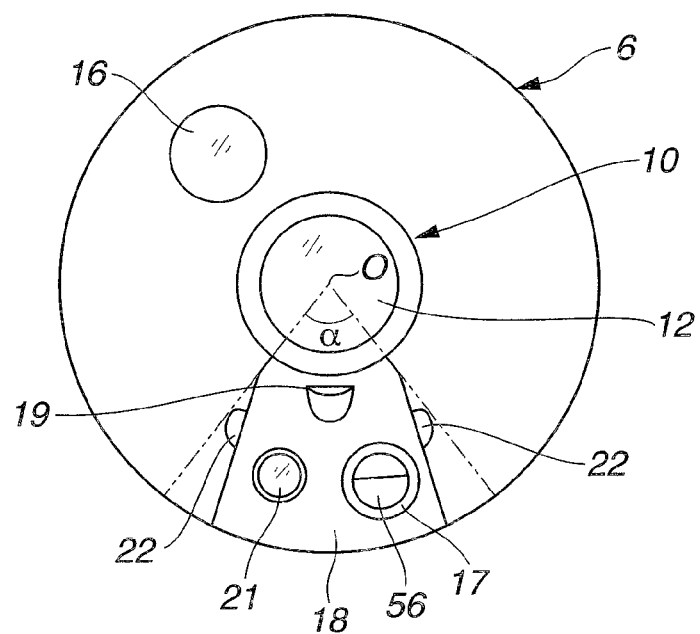
FIG. 8 is a front view illustrating a configuration of the distal end portion.

Next, a second embodiment of the present invention will be described. FIG. 7 shows a perspective view of a structure in the vicinity of a distal end of an insertion portion 4 of an endoscope of the second embodiment of the present invention and FIG. 8 illustrates a front view thereof.

The present embodiment basically has a configuration equivalent to the endoscope 2 of the first embodiment with the distal end portion 6 partially modified. There are provided a cylindrical portion 10 protruding in a cylindrical shape from a center position of the distal end face and a support portion 18 provided with shielding section 18a that supports protruding members such as a forward viewing observation window nozzle portion 19 and shields (provides light-shielding of) the protruding members so as not to appear within a side viewing field of a side viewing observation window 13 on the distal end face of the distal end portion 6.

As with the first embodiment, the cylindrical portion 10 is provided with a forward viewing observation window 12, the side viewing observation window 13 and a side viewing illuminating window 14. The present embodiment shows an example where the outside diameter of the side viewing illuminating window 14 is the same as the outside diameter of the side viewing observation window 13, but the outside diameters may be different. Furthermore, in the present embodiment, the side viewing illuminating window 14 is configured to be able to illuminate the entire sideward perimeter. Of course, the same configuration as that of the first embodiment may also be adopted.

In the first embodiment, the channel distal end opening portion 17 opens on the distal end face of the distal end portion 6, whereas the present embodiment adopts a configuration in which the channel distal end opening portion 17 is provided in the support portion 18 in which the shielding section 18a is formed.

The channel distal end opening portion 17 communicates with a conduit 17b that forms a channel provided inside the insertion portion 4 (including the distal end portion 6) via a conduit 17a inside the support portion 18.

Furthermore, although the cylindrical portion 10 is provided at a position decentered from the center position of the distal end portion 6 according to the first embodiment, the cylindrical portion 10 is provided in the center position of the distal end portion 6 in the present embodiment.

Furthermore, although the support portion 18 is provided in a direction slightly deviated from the direction right below the cylindrical portion 10 in the first embodiment, the support portion 18 is provided in a direction right below the cylindrical portion 10 in the present embodiment.

Furthermore, as with the first embodiment, the forward viewing illuminating window 16 is provided on the distal end face of the distal end portion 6, but the forward viewing illuminating window 16 is provided in a position closer to the top in the present embodiment.

As shown in FIG. 8, the shielding section 18a of the support portion 18 provides shielding, for example, at an angle of α around an optical axis of an objective optical system 11, that is, an image pickup center O in the circumferential direction. A forward viewing observation window nozzle portion 19, a forward viewing illuminating window 21, a side viewing observation window nozzle portion 22 and the channel distal end opening portion 17 are provided in the support portion 18 so as to fall within the angle of α. The rest of the configuration is similar to that of the first embodiment.

The present embodiment basically has effects similar to those of the first embodiment, but has operations or effects different from the operations or effects when a treatment instrument is used.

In the first embodiment, when the surgeon causes the treatment instrument to protrude from the channel distal end opening portion 17, the protruding treatment instrument appears within the side viewing field of the side viewing observation window 13, and therefore the treatment instrument is observed as a side viewing field image.

By contrast, in the present embodiment, the portion of the conduit 17a into which the treatment instrument is inserted that appears within the side viewing field of the side viewing observation window 13 is shielded by the shielding section 18a, and therefore even when the treatment instrument is inserted, this does not appear in a side viewing field image. For example, FIG. 7 illustrates the distal end portion of a treatment instrument 56 protruding up to the vicinity of the channel distal end opening portion 17, but the distal end side of the treatment instrument 56 does not appear in a side viewing field image.

The distal end side of the treatment instrument 56 has a high function of reflecting light, and therefore if this enters the side viewing field just near the side viewing observation window 13, a high luminance image results, and thus if a condition is set for performing automatic light adjustment, the function of automatic light adjustment is reduced. Furthermore, the high luminance may produce flare in the endoscope image which is an observed image.

Therefore, even when the treatment instrument 56 is used, according to the present embodiment, an excellent endoscope image can be obtained and also the automatic light adjustment function can be used without deterioration.

Figure 9:
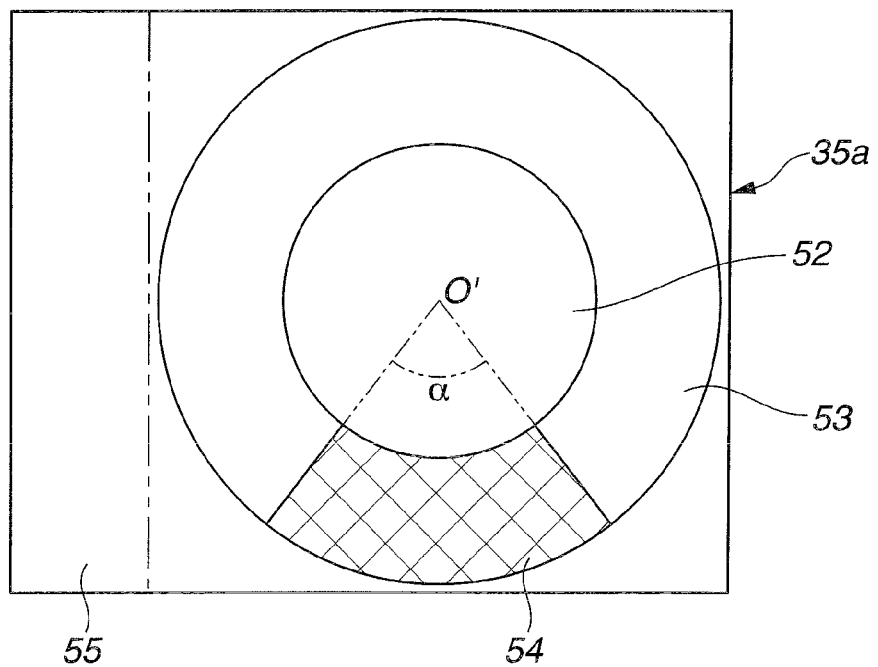
FIG. 9 is a diagram illustrating an example of an endoscope image according to the second embodiment.

The endoscope image displayed on a display surface 35a of a monitor 35 of the present embodiment is as shown in FIG. 9. Since FIG. 9 bears close resemblance to the case in FIG. 6, components are shown assigned the same reference numerals as those in FIG. 6.

The present embodiment has effects similar to those of the first embodiment. Furthermore, also even when the treatment instrument 56 is used, it is possible to obtain an endoscope image having an excellent side viewing field image.

To be more specific, according to the present embodiment, the shielding section 18a of the support portion 18 shields the forward viewing observation window nozzle portion 19, the forward viewing illuminating window 21, the side viewing observation window nozzle portion 22 and the conduit 17a into which the treatment instrument 56 is inserted as protruding members different from the original observation target appearing within the side viewing field of the side viewing observation window 13 so as not to be acquired as side viewing field images, and it is thereby possible to generate an excellent side viewing field image.

Therefore, the surgeon observes an endoscope image having an excellent side viewing field image, and can thereby smoothly perform an inspection of tubular organs or the like.

Furthermore, according to the present embodiment, when the treatment instrument 56 is used, and even if an image signal of the image pickup device 34 is used for automatic light adjustment, the image signal of the side viewing field image is an image signal not affected by the protruding member, and therefore automatic light adjustment can be effectively used without deterioration of the function.

The outside diameter of the support portion 18 need not be the same as the outside diameter of the distal end portion 6. Furthermore, although the support portion 18 is provided at one location in the direction below the cylindrical portion 10, the support portions 18 may also be provided at a plurality of locations.

Furthermore, when the distal end side of the treatment instrument 56 is made to protrude further toward the distal end side so as to fall within the forward viewing field of the forward viewing observation window 12, it is possible to observe the distal end side of the treatment instrument 56 through the forward viewing observation window 12.

In this case, the luminance level of the image signal of the forward viewing field image is influenced by the high luminance portion of the distal end side of the treatment instrument 56, but at least the side viewing field image is designed not to be thereby influenced and there is an effect of being able to reduce the influences compared to the case where both images have influences.

(Third Embodiment)

Figure 10:
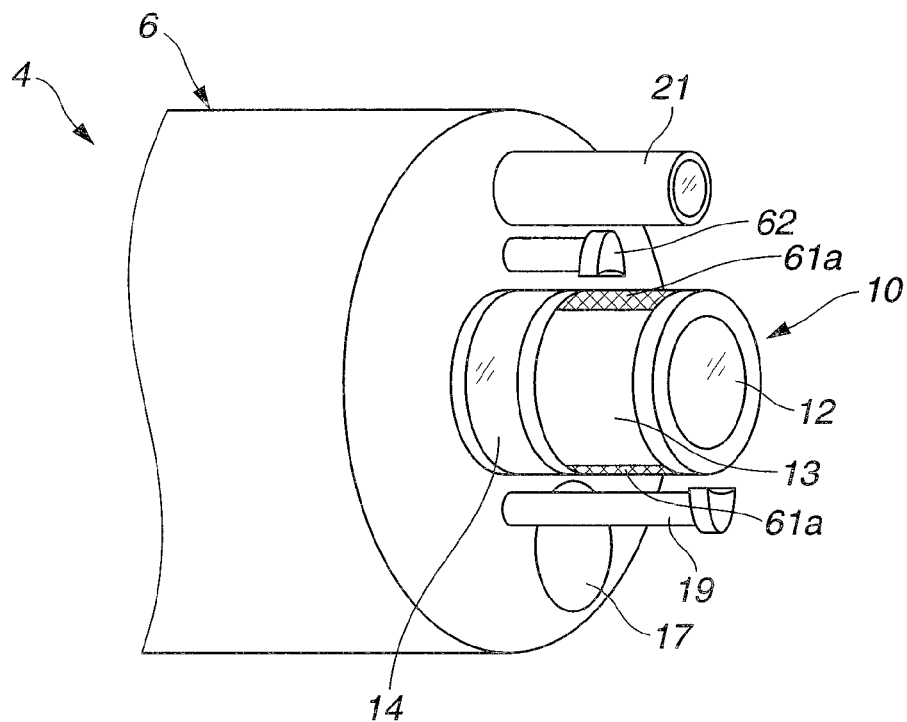
FIG. 10 is a perspective view illustrating a configuration of a distal end portion according to a third embodiment of the present invention.
Figure 11:
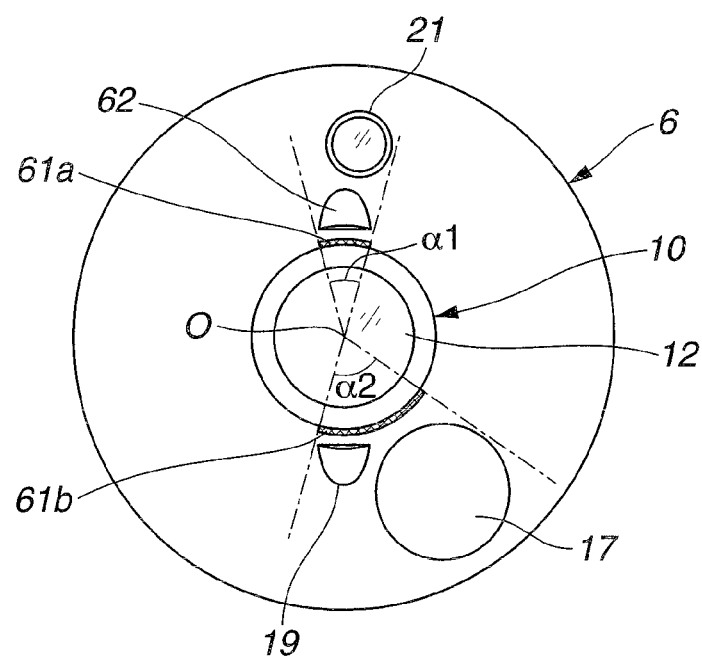
FIG. 11 is a front view illustrating a configuration of the distal end portion.

Next, a third embodiment of the present invention will be described. FIG. 10 illustrates a perspective view of a configuration in the vicinity of a distal end portion 6 of an insertion portion 4 of an endoscope of the third embodiment of the present invention and FIG. 11 illustrates a front view thereof.

The present embodiment provides shielding sections 61a and 61b on the outer surface of a side viewing observation window 13 so that light from protruding members that protrude from the distal end face of the distal end portion 6 and enter the side viewing field of the side viewing observation window 13 does not enter the side viewing field of the side viewing observation window 13.

A cylindrical portion 10 having a cylindrical shape is provided in the center of the distal end face of the distal end portion 6. As with the second embodiment, the cylindrical portion 10 is provided with a forward viewing observation window 12, the side viewing observation window 13 and a side viewing illuminating window 14.

A side viewing observation window nozzle portion 62 and a forward viewing illuminating window 21 are provided as protruding members so as to protrude at positions in the upper part of the cylindrical portion 10 on the distal end face of the distal end portion 6 and furthermore, a forward viewing observation window nozzle portion 19 is provided as a protruding member so as to protrude at a position in the lower part of the cylindrical portion 10. Furthermore, a channel distal end opening portion 17 is provided neighboring the forward viewing observation window nozzle portion 19 on the distal end face of the distal end portion 6.

Furthermore, the shielding sections 61a and 61b for shielding light from the protruding members so as not to enter the side viewing field of the side viewing observation window 13 are provided on the side of the upper part and the side of the lower part provided with the protruding members of the side viewing observation window 13.

Although the shielding sections 61a and 61b can be made up of a film-like member by applying a black paint to the side viewing observation window 13 in a film shape, the present invention is not limited thereto, but a metal having a high light-shielding function or the like may be formed in a film shape through vapor deposition on the side viewing observation window 13 or a black sheet or a sheet having a high light-shielding function may be adhered and attached to the side viewing observation window 13.

As shown in FIG. 11, the shielding sections 61a and 61b provide shielding at angles α1 and α2 respectively around an image pickup center O. Therefore, light from the side viewing observation window nozzle portion 62 and the forward viewing illumination section 63 is shielded by the shielding section 61a and light from the forward viewing observation window nozzle portion 19 is shielded by the shielding section 61b and does not enter the side viewing observation window 13.

Furthermore, according to the present embodiment, also even when a treatment instrument protrudes from the channel distal end opening portion 17, light from the treatment instrument can be shielded by the shielding section 61b. The rest of the configuration is similar to that of the aforementioned first or second embodiment.

Figure 12:
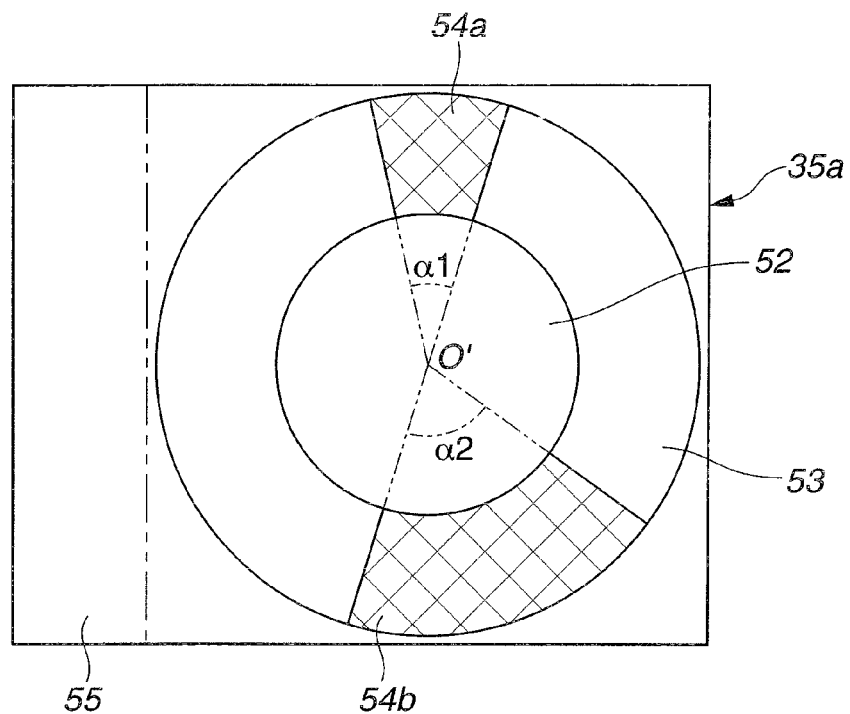
FIG. 12 is a diagram illustrating an example of an endoscope image according to the third embodiment.

An endoscope image displayed on a display surface 35a of a monitor 35 in the case of the present embodiment is as shown in FIG. 12. As shown in FIG. 12, shielding regions 54a and 54b corresponding to the shielding sections 61a and 61b shown in FIG. 11 are formed in a display region 53 of the side viewing field image.

In substantially the same way as the second embodiment, according to the present embodiment, the protruding members that protrude from the distal end face of the distal end portion 6 are shielded so as not to be acquired by the side viewing observation window 13 as an image, and thereby an endoscope image having an excellent side viewing field image can be acquired.

Furthermore, even when the treatment instrument is used and the distal end side of the treatment instrument is made to protrude from the channel distal end opening portion 17, shielding can be provided by the shielding section 61b, and it is thereby possible to prevent the occurrence of flare and use automatic light adjustment without deterioration of the function.

Furthermore, according to the present embodiment, the film-like shielding sections 61a and 61b are provided in the side viewing observation window 13, and thereby effects similar to those of the second embodiment are realized at low cost (except the support function).

Figure 13:
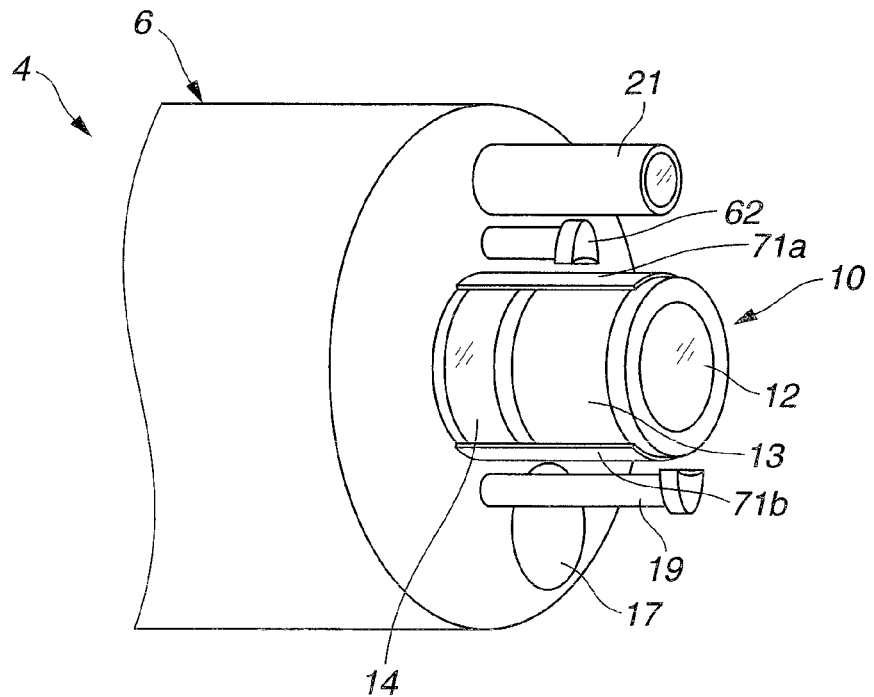
FIG. 13 is a perspective view illustrating a configuration of a distal end portion according to a modification example of the third embodiment.

FIG. 13 illustrates a configuration of a distal end portion 6 of an insertion portion 4 of an endoscope according to a first modification example of the present embodiment. The present modification example adopts a configuration replacing the aforementioned film-like shielding sections 61a and 61b provided in the side viewing observation window 13 by shielding plates 71a and 71b having a shielding function protruding toward the distal end side more than the side viewing observation window 13 along the side of the cylindrical portion 10 from the distal end face of the distal end portion 6.

That is, the shielding plates 71a and 71b are arranged over the entire viewing field from the proximal end side to the distal end side of the side viewing observation window 13, that is, from the side viewing rear side to the side viewing forward side of the side viewing observation window 13.

In this case the shielding plates 71a and 71b, and the side viewing observation window 13 may be adhered together using an adhesive. Furthermore, delustering or lusterless paint may be applied to the inner surface on the side viewing observation window 13 side of the shielding plates 71a and 71b. Furthermore, as described above, a metal such as stainless steel having a high light-shielding function or resin such as polysulfone resin provided with a light-shielding function may be used. The present modification example has substantially the same effect as that of the third embodiment.

As a second modification example of the present embodiment, the shielding section 61b may be formed to prevent light from the forward viewing observation window nozzle portion 19 from entering the side viewing observation window 13. In the case of the present modification example, when a treatment instrument is used, the treatment instrument exerts an influence, but in the case of application with a small frequency of use of the treatment instrument, a side viewing observation window having a wider side viewing field can be realized.

Furthermore, the present second modification example may be applied to the above described first modification example.

(Fourth Embodiment)

Figure 14:
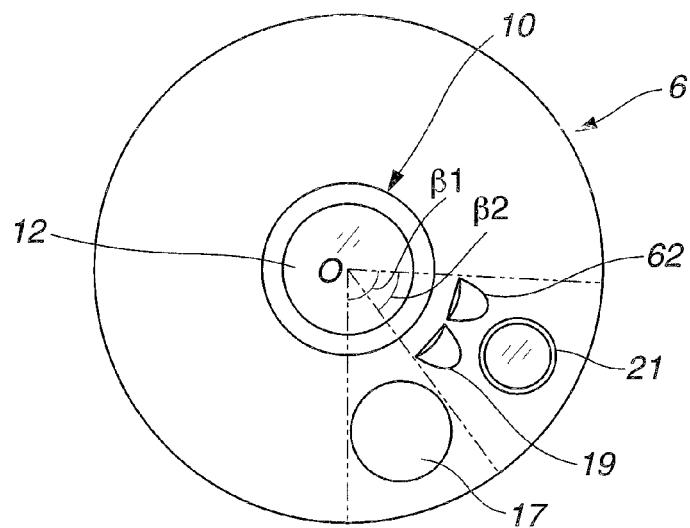
FIG. 14 is a front view illustrating a configuration of a distal end portion according to a fourth embodiment of the present invention.

Next, a fourth embodiment of the present invention will be described. FIG. 14 illustrates a front view of a distal end portion 6 of an insertion portion 4 of an endoscope according to the fourth embodiment of the present invention.

A cylindrical portion 10 is provided in the center of a distal end face of the distal end portion 6 and a channel distal end opening portion 17 is provided therebelow. Furthermore, a forward viewing observation window nozzle section 19, a side viewing observation window nozzle portion 62 and a forward viewing illuminating window 21 are provided so as to protrude as protruding members at diagonally lower positions neighboring the cylindrical portion 10 on the distal end face of the distal end portion 6.

These protruding members and the channel distal end opening portion 17 are arranged within an angle of, for example, β1 around an image pickup center O and the protruding members alone are arranged within an angle of β2 around the image pickup center O.

Figure 15:
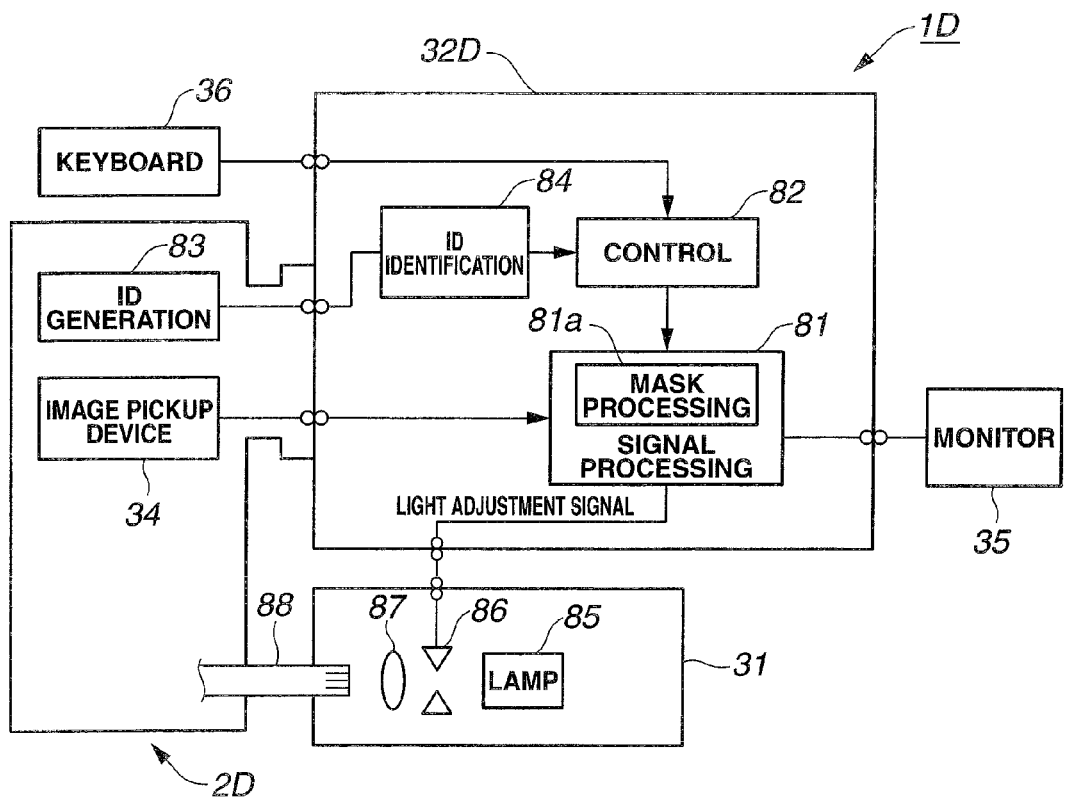
FIG. 15 is a block diagram illustrating a schematic configuration of the endoscope apparatus.

On the other hand, a video processor 32D as an image processing apparatus to which an endoscope 2D provided with the distal end portion 6 is detachably connected incorporates a signal processing section 81 that performs signal processing on an image signal outputted from an image pickup device 34 as shown in FIG. 15 and the video signal as an image signal for display generated by the signal processing section 81 is outputted to a monitor 35. The endoscope having an insertion portion 4 provided with a distal end portion different from the arrangement structure of the distal end portion 6 shown in FIG. 14 is also detachably connected to the video processor 32D.

The signal processing section 81 is provided with a mask processing section 81a that performs signal processing (referred to as "mask processing") of electrically masking (shielding) a portion corresponding to the protruding member of the image signal portion by the side viewing observation window 13 in the image signal of the image pickup device 34. The mask processing section 81a performs mask processing corresponding to a control signal from a control section 82.

Furthermore, the endoscope 2D has an ID generation section 83 that generates identification information (ID information) specific to the endoscope 2D and when the endoscope 2D is connected to the video processor 32D, the ID information is inputted to an ID identification section 84 provided in the video processor 32D.

The ID identification section 84 sends the identified ID information to the control section 82 and the control section 82 generates a control signal corresponding to the ID information and controls mask processing of the mask processing section 81a.

The ID information includes arrangement information of protruding members and the channel distal end opening portion 17 appearing in the side viewing field in the distal end portion 6 of the endoscope 2D and the mask processing section 81a performs mask processing corresponding to the arrangement information of the protruding members and channel distal end opening portion 17 based on the ID information.

A configuration may also be adopted which includes inside the video processor 32D (e.g., inside the mask processing section 81a) arrangement information recording means such as a lookup table for reading arrangement information of the protruding members and channel distal end opening portion 17 appearing in the side viewing field of the distal end portion 6 of the endoscope 2D for which the ID information is generated from the ID information.

When the treatment instrument is not inserted into the channel, the treatment instrument protruding from the channel does not appear in the side viewing field. For this reason, the mask processing section 81a performs mask processing corresponding to the arrangement information of at least the protruding members based on the ID information so as to allow the operator to select whether or not to perform mask processing corresponding to the arrangement information of the channel distal end opening portion 17.

Furthermore, the control section 82 is connected to an input apparatus such as a keyboard 36 and the operator such as the surgeon can input from the keyboard 36 an instruction on ON/OFF of mask processing operation, mask shape generated through mask processing and mask region or the like and the control section 82 controls the operation of the mask processing section 81a in accordance with the instruction inputted.

Therefore, the input apparatus such as the keyboard 36 has the function of switching instruction means for instructing switching ON/OFF the mask processing operation. The video processor 32D including the keyboard 36 has the function of switching means for switching ON/OFF the mask processing operation.

The input apparatus as the switching instruction means may also be a foot switch, a switch on the operation panel of the video processor or a scope switch 25 or the like in addition to the keyboard 36.

The signal processing section 81 outputs a video signal corresponding to the mask processing by the mask processing section 81a to the monitor 35. Furthermore, the signal processing section 81 calculates average luminance subjected to mask processing and outputs a light adjustment signal for light adjustment of the light to appropriate brightness to a light source apparatus 31. The signal processing section 81 outputs, for example, a difference signal from a reference brightness value corresponding to appropriate brightness to the light source apparatus 31 as a light adjustment signal.

The light source apparatus 31 adjusts the light quantity from a lamp 85 as a light source using a diaphragm 86 that can adjust the amount of opening/closing, condenses the light using a lens 87 and supplies the light to a light guide 88 as a light guide member of illuminating light. In this case, by automatically adjusting the amount of opening/closing of the diaphragm 86 through a light adjustment signal, the quantity of illuminating light supplied to the light guide 88 is automatically adjusted (automatic light adjustment).

By automatically adjusting the amount of opening/closing of the diaphragm 86 through the light adjustment signal in this way, the amount of illuminating light supplied to the light guide 88 is adjusted so as to maintain the brightness value (luminance level) in the case of appropriate brightness.

When, for example, the average luminance level of the endoscope image displayed is brighter than a brightness value in the case of appropriate brightness, the amount of opening/closing of the diaphragm 86 is controlled so as to decrease through a light adjustment signal in that case and adjusted so as to maintain the brightness value in the case of appropriate brightness.

Figure 16A:
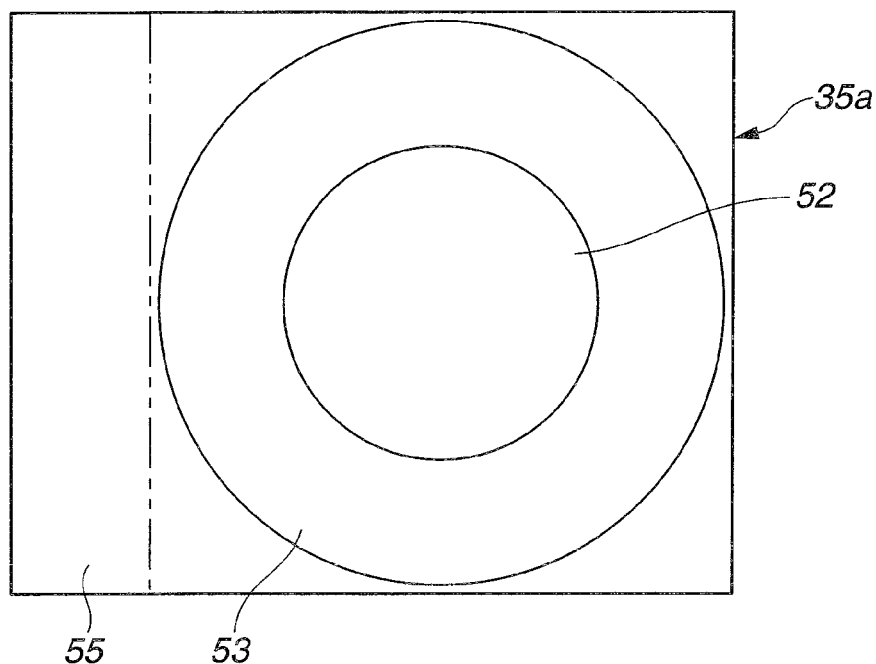
FIG. 16A is a diagram illustrating an example of endoscope image when mask processing is set to OFF.

FIG. 16A shows an endoscope image when mask processing by the mask processing section 81a is set to OFF. In this case, the endoscope image not under mask processing is displayed in a display region 52 for forward viewing field images and a display region 53 for side viewing field images.

Figure 16B:
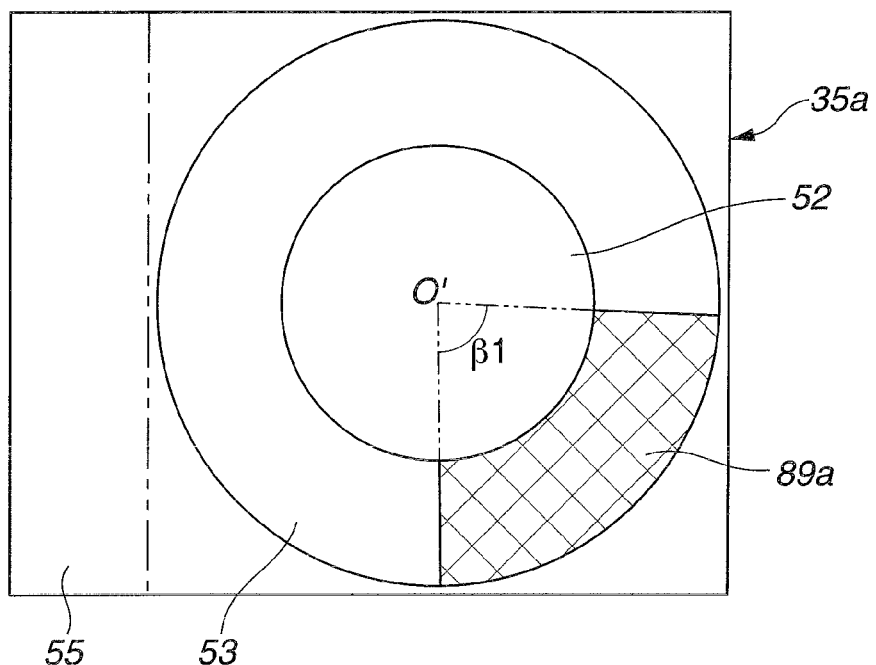

On the other hand, FIG. 16B illustrates an endoscope image when mask processing corresponding to ID information by the ID generation section 83 is applied. In the case of FIG. 16B, in correspondence with the arrangement information of the protruding members and channel distal end opening portion 17, the display region portion in which the protruding members and the channel distal end opening portion 17 are displayed in the display region 53 for side viewing field images constitutes a masked section 89a where those images are electrically masked which is anon-display region where no image in the region of the masked section 89a is displayed.

Thus, according to the present embodiment, it is possible to shield images of protruding members appearing in the side viewing field of the side viewing observation window 13 through electric signal processing on as not to be displayed in an endoscope image.

Therefore, as the endoscope image displayed on the monitor 35, the present embodiment has effects similar to those when shielding is provided by the shielding section provided on the endoscope side as with the aforementioned first to third embodiments.

Furthermore, the present embodiment adopts the configuration in which a light adjustment signal can be generated from a video signal subjected to mask processing, and can thereby use the light adjustment function not only for protruding members but also when the treatment instrument is used without deterioration of the light adjustment function.

As a supplementary explanation, as described in the section of related arts, when the nozzle as a protruding member appears in a side viewing field image of short distance, the luminance level of an image signal (video signal) of the image of the original observation target rises due to the image of the nozzle, deteriorating the light adjustment function. However, the present embodiment generates a light adjustment signal from a video signal obtained by applying mask processing to the image of the protruding member in the side viewing field image, and can thereby prevent deterioration of the light adjustment function. Furthermore, even when the treatment instrument protrudes from the channel distal end opening portion 17, this functions as in the case of the protruding member. This treatment instrument can also be regarded as a protruding member.

Figure 17:
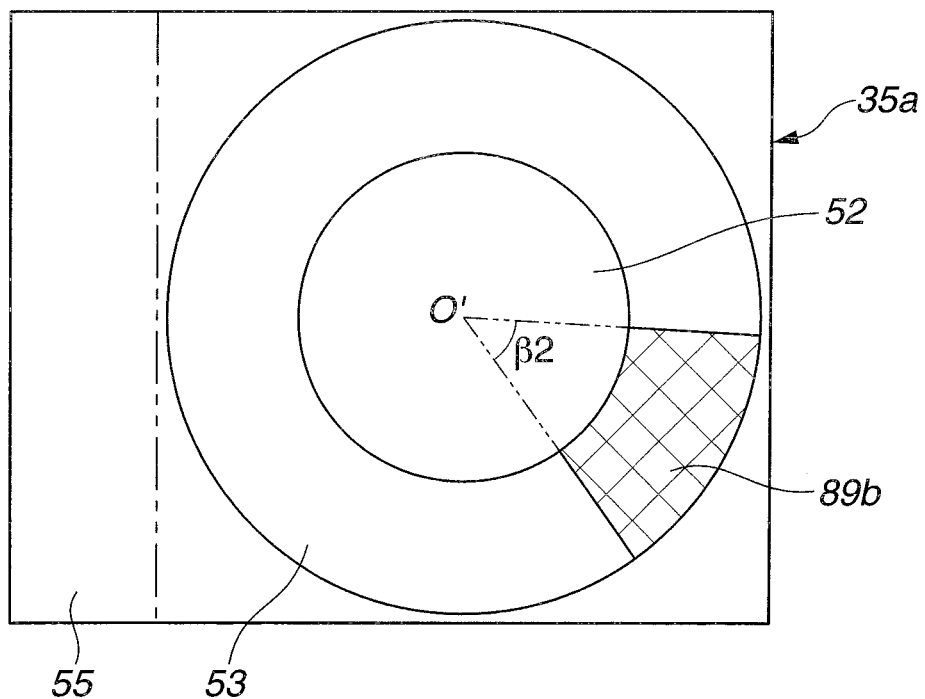
FIG. 17 is a diagram illustrating an example of endoscope image when set to mask processing corresponding to arrangement information of a protruding member.

Furthermore, in the present embodiment, the surgeon can input an instruction so as to perform mask processing corresponding to the arrangement information of only the protruding members from the keyboard 36. When this instruction is inputted, as shown in FIG. 17, it is possible to form a non-display region by a masked section 89b corresponding to the arrangement information of only the protruding members.

Therefore, when not using any treatment instrument, if the surgeon inputs an instruction so as to generate the masked section 89b corresponding to the arrangement information of only the protruding members, the display region of the side viewing field image can be broadened.

Furthermore, in the case of an endoscope where the endoscope itself does not have the function of the shielding section, if the surgeon inputs an instruction so as to perform mask processing appropriate for the endoscope from the input apparatus such as the keyboard 36, the mask processing section 81a generates a masked section subjected to mask processing in accordance with the instruction inputted. Therefore, the surgeon can generate a desired masked section and perform endoscopy with the endoscope image in which the masked section is formed. Thus, the present embodiment enables the region in which a masked section is formed to be changed.

An embodiment configured by partially combining the aforementioned embodiments or the like also belongs to the present invention. For example, it is possible to adopt a configuration combining the fourth embodiment with the first to third embodiment(s). Such a configuration may include a configuration where the protruding members appearing in the side viewing field image are mechanically shielded on the endoscope side and a configuration where the protruding members are electrically shielded on the image processing apparatus side.

For example, in the endoscope having the configuration shown in FIG. 13, a shielding section for mechanical shielding is formed of the shielding plates 71a and 71b provided on the endoscope, but in the case of an endoscope not provided with the shielding plates 71a and 71h, electrical shielding is provided on the image processing apparatus side.

Furthermore, for example, in the endoscope having the configuration shown in FIG. 13, when the treatment instrument protrudes from the channel distal end opening portion 17 and this treatment instrument constitutes a protruding member, the treatment instrument can be electrically shielded on the image processing apparatus side by inputting an instruction for performing mask processing from the keyboard 36.

What is claimed is:

1. An endoscope apparatus comprising:
   an insertion portion inserted into an observation target;
   a side viewing observation section provided on a distal end side of the insertion portion for acquiring a subject image of an observation target in a circumferential direction of the insertion portion;
   a forward viewing observation section provided closer to the distal end side than the side viewing observation section of the insertion portion for acquiring a subject image of an observation target in an insertion direction of the insertion portion;
   a shielding section that forms a shielding region for electrically shielding a display of a part of the subject within a viewing field of the side viewing observation section;
   an image processing apparatus that generates a side viewing observed image and a forward viewing observed image including the shielding region as observed images based on the subject image in the circumferential direction obtained from the side viewing observation section and the subject image in the insertion direction obtained from the forward viewing observation section; and
   a cleaning nozzle arranged within the shielding region and protruding from the insertion portion, for cleaning the forward viewing observation section and/or the side viewing observation section.

2. The endoscope apparatus according to claim 1, wherein the shielding section comprises a mask processing section provided in the image processing apparatus that forms, as the shielding region, a masked section electrically shielded through signal processing on an image portion in a range in which the nozzle is located on the side viewing observed image generated by the image processing apparatus.

3. The endoscope apparatus according to claim 2, wherein an endoscope having the insertion portion is detachably connected to the image processing apparatus, and
   the mask processing section can change a region in which the masked section is formed according to identification information specific to the endoscope connected to the image processing apparatus.

4. The endoscope apparatus according to claim 3, wherein the image processing apparatus further comprises a switching section that switches between processing that forms the masked section and processing that does not form the masked section.

5. The endoscope apparatus according to claim 2, wherein the side viewing observation section and the forward viewing observation section protrude from a distal end face of the insertion portion, and are provided in a cylindrical member having a smaller diameter than an outside diameter of the insertion portion, the cylindrical member further comprises an objective optical system comprising:
a rotationally symmetric first lens arranged along a central axis of the cylindrical member for forming a subject image in the insertion direction; and
a second lens arranged behind the first lens and connected to a mirror lens having a mirror surface for refracting light passing through the first lens and forming a subject image in the insertion direction and forming a subject image in the circumferential direction, and
an image pickup surface of an image pickup device is arranged at an image forming position of the objective optical system.

6. The endoscope apparatus according to claim 5, wherein the objective optical system forms a subject image in the insertion direction in a circular region in a center of the image pickup surface of the image pickup device and forms a subject image in the circumferential direction in a ring region of an outer circumference of the circular region, and the image processing apparatus generates the forward viewing observed image and the side viewing observed image from image signals of the circular region and the ring region photoelectrically converted by the image pickup device.

7. An endoscope comprising:
an insertion portion inserted into an observation target;
a side viewing observation section provided on a distal end side of the insertion portion for allowing light from the observation target in a circumferential direction of the insertion portion to enter and acquiring a subject image;
a forward viewing observation section provided closer to a distal end side than the side viewing observation section in the insertion portion for allowing light from the observation target in an insertion direction of the insertion portion to enter and acquiring a subject image;
a support portion protruding in a distal end direction of the insertion portion, the support portion neighboring the side viewing observation section and being provided so as to be located within a viewing field of the side viewing observation section;
a shielding section provided to the support portion so as to neighbor the side viewing observation section, for shielding light from the subject entering the side viewing observation section; and
a cleaning nozzle provided so as to protrude from the support portion and arranged within a shielding region formed by the shielding section, for cleaning the forward viewing observation section and/or the side viewing observation section.

8. The endoscope according to claim 7, wherein the shielding section is disposed at a predetermined position inside the side viewing observation section over an entire length at least from a proximal end to a distal end of the side viewing observation section.

9. The endoscope according to claim 8, wherein the support portion comprises a conduit into which a treatment instrument is inserted and an opening portion that communicates with the conduit and opens at an end face closer to the distal end side than the side viewing observation section, and the treatment instrument is inserted into the conduit to protrude up to within the viewing field of the forward viewing observation section.

10. The endoscope according to claim 8, wherein the side viewing observation section comprises a ring-shaped observation window formed on an entire perimeter of a side of the insertion portion except for the shielding section.

11. The endoscope according to claim 10, wherein the shielding section is made of a light-shielding film-like member arranged on an outer surface of the ring-shaped observation window.

12. The endoscope according to claim 11, wherein the side viewing observation section and the forward viewing observation section protrude from a distal end face of the insertion portion, and are provided in a cylindrical member having a smaller diameter than an outside diameter of the insertion portion, the cylindrical member further comprises an objective optical system comprising:
a rotationally symmetric first lens arranged along a central axis of the cylindrical member for forming a subject image in the insertion direction; and
a second lens arranged behind the first lens and connected to a mirror lens having a mirror surface for refracting light passing through the first lens and forming a subject image in the insertion direction and forming a subject image in the circumferential direction, and
an image pickup surface of an image pickup device is arranged at an image forming position of the objective optical system.

13. The endoscope apparatus according to claim 12, wherein the objective optical system forms a subject image in the insertion direction in a circular region in a center of the image pickup surface of the image pickup device and forms a subject image in the circumferential direction in a ring region of an outer circumference of the circular region, and the endoscope further comprises an image processing apparatus for generating a forward viewing observed image and a side viewing observed image from image signals of the circular region and the ring region photoelectrically converted by the image pickup device.

* * * * *